United States Patent

Halgren et al.

[11] Patent Number: 5,851,477
[45] Date of Patent: Dec. 22, 1998

[54] REINFORCED TUBING MANUFACTURE BY A PLASTIC PROCESSING SCREW MACHINE

[76] Inventors: Donald N. Halgren, 35 Central St.; Desider G. Csongor, 19 Bennett St., both of Manchester, Mass. 01944

[21] Appl. No.: 778,947

[22] Filed: Jan. 6, 1997

Related U.S. Application Data

[63] Continuation-in-part of Ser. No. 773,875, Dec. 30, 1996, Pat. No. 5,744,092, which is a continuation-in-part of Ser. No. 511,055, Aug. 3, 1995, Pat. No. 5,670,112, which is a continuation-in-part of Ser. No. 393,200, Feb. 23, 1995, abandoned.

[51] Int. Cl.$^6$ .................................................. B29C 47/06
[52] U.S. Cl. .................... 264/512; 264/103; 264/171.12; 264/515; 425/113
[58] Field of Search ..................... 264/572, 513, 264/515, 45.1, 50, 241, 255, 103, 171.12, 171.13, 171.16, 171.2, 512; 425/113

[56] References Cited

U.S. PATENT DOCUMENTS

| 466,910 | 1/1892 | Royle et al. ........................ 425/113 |
| 815,571 | 3/1906 | Williams ............................. 425/114 |
| 3,296,659 | 1/1967 | Okazaki ............................. 425/112 |
| 3,566,753 | 3/1971 | Mantke ............................. 425/113 |
| 4,172,106 | 10/1979 | Lewis ............................. 264/171.16 |
| 4,472,126 | 9/1984 | Mitsui et al. ..................... 264/103 |
| 4,517,039 | 5/1985 | Satzler ............................. 264/102 |

*Primary Examiner*—Catherine Timm
*Attorney, Agent, or Firm*—Don Halgren

[57] ABSTRACT

The invention comprises a plasticating machine for the working and forcing of plastic material into a mold, said machine including an elongated housing having a first or proximal end and a second or distal end and an elongated screw shaft with a screw flight therearound, the screw shaft being rotatably supported in the elongated housing, for the working of plastic between the screw shaft and the elongated housing. At least one pair of coaxial spaced apart delivery conduits are generally longitudinally arranged through the screw shaft, from a proximal end to a distal tip end thereof. A tubular mesh generating apparatus is arranged at the distal end of the coaxially conduits to generate/weave and feed a tubular reinforcement mesh along the length of the annular delivery channel to a plastic melt at its distalmost end. A movable forming tool is supported adjacent the distal end of the innermost conduit of the coaxial conduits. The mesh is arranged to be movable with respect to the screw shaft and over the forming tool, to engage any thermoplastic material being driven from between the screw shaft and the barrel housing to form a reinforced tubular product such as a pipe or tube, as it is driven through a die at the distal end of the machine.

7 Claims, 2 Drawing Sheets

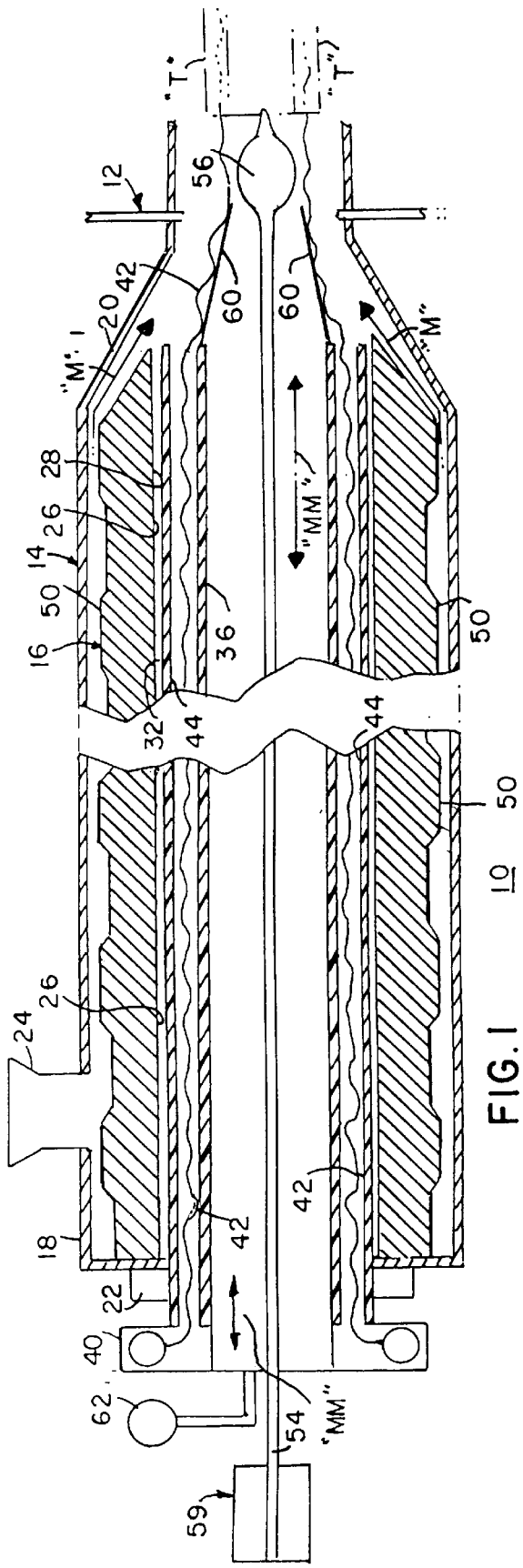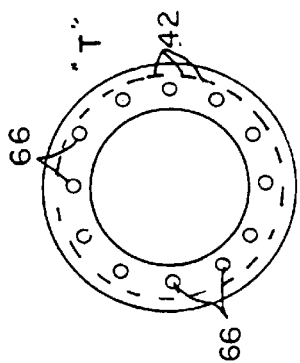

REINFORCED TUBING MANUFACTURE BY A PLASTIC PROCESSING SCREW MACHINE

RELATED INVENTIONS

The present invention relates to a method for molding products from a plastic material, this Application being a Continuation-In-Part Application of U.S. patent application Ser. No. 08/773,875, filed Dec. 30, 1996, now U.S. Pat. No. 5,744,092, which is a Continuation-In-Part Application of U.S. application Ser. No. 08/511,055, filed Aug. 3, 1995, now U.S. Pat. No. 5,670,112, which is a Continuation-In-Part Application of U.S. application Ser. No. 08/393,200, filed Feb. 23, 1995, now abandoned, each of which are incorporated herein by reference.

BACKGROUND OF THE INVENTION

1. Field of the Invention

This invention relates to plastic processing machines, and more particularly to moveable screw arrangements for the manufacture of reinforced tubing.

2. Prior Art

The manufacture of pipes generally, or more particularly a narrow flexible tubing, such as the type that may be utilized for medical procedures particularly, for catheter shafts or the like, is very difficult. Such medical tubing needs to be of generally uniform wall thickness (of minimal outside diameter such as about 7 to about 13 French with internal diameter of only several thousandths of an inch), which wall thickness must be able to travel into narrow veins, arteries or the like. Such tubes must therefore exhibit columnar strength, and be torquable to permit a near 1 to 1 angular turning at a distant tip located deep within a body vessel, from a proximal end of that shaft at a location outside of that body. Such turning is required to permit a physician to push such a shaft into branch arteries and veins to reach the location of vessel treatment. Such walls need to be relatively smooth so as to not hinder the pushing of the tube in any artery or vein, and to minimize turbulence which the surfaces of the tube walls may generate.

Limitations of present tube manufacture machinery do not permit the introduction of a flexible reinforcement into the flexible wall of a thermoplastic tube being manufactured as that thermoplastic material is going into a mold or die. as well as does the present invention.

It is therefore an object of the present invention, to provide a plasticating screw machine having capabilities not found in the prior art.

It is a further object of the present invention, to provide a screw machine which is able to present a flexible reinforcment and/or a gas, simultaneously or sequentially into a thermoplastic material being molded and/or extruded into a tubular form.

It is yet a further object of the present invention, to provide an arrangement which permits the rapid cooling and completion of a plastic part in a manner not found in the prior art.

BRIEF SUMMARY OF THE INVENTION

The present invention relates to a plasticating screw machine for the manufacture of flexible tubing utilizing thermoplastic material and pressurizably directing that thermoplastic material with a reinforcing web and into an extrusion die.

The plasticating screw machine of the present invention comprises an external barrel shaped housing having an elongated screw shaft rotatively supported therewithin. The housing and the screw shaft have a proximal or first end and a distal or a second end. The screw shaft is rotatively empowered at the proximal first end of the housing by a motor drive means thereattached. At least one material in-feed supply hopper may be arranged through the housing near the proximal end thereof.

The screw shaft has a bore extending completely therethrough along its longitudinal axis, from its proximalmost end to its distalmost end. The bore has a wall surface which may be rifled, that is, it may a spiral groove cut within its surface, to define a material moving path.

An outer non-rotational tubularly shaped sleeve support may be arranged within the bore of the screw shaft, extending preferably from the proximal end of the housing, to the distal end of the shaft. An inner tubularly shaped sleeve support may be arranged coaxially within the outer sleeve support within the bore of the screw shaft. A tubular web generating or weaving apparatus is disposed around the periphery of the proximal end of the inner sleeve support, so as to generate, knit, mold or weave a tubular web of mesh reinforcement thereat, preferably the mesh or web being formed of metal wire of stainless steel, nickel-titanium or an alloy thereof, or of a reinforcing plastic film with or without openings therethrough, which web mesh is directed into the annular path spaced between the inner sleeve support and the outer sleeve support.

The web mesh extends into and travels through the bore of the plasticating screw screw shaft, within the annular channel defined by the inner and outer support sleeves, and is driven from the distal end of those inner and outer sleeve supports into the distal discharge end of the screw shaft and screw housing, which may include the flow path of thermoplastic material being worked between the helical screw flight on the screw shaft and the inner walls of the barrel housing. The web mesh and the thermoplastic material mix into the desired tubular shape of an extruded shaft or pipe. A mandrel holding shaft preferrably extends through the center of the inner sleeve support, with a mandrel forming tool on its distalmost end thereof. The mandrel forming tool itself may extend beyond the distalmost end of the inner sleeve support, to provide the needed shape to the inner surface of the tubing being extruded from the machine.

The mandrel support shaft and attached mandrel, may both be hollow to permit the supply of a pressurized fluid downstream therein, to cool, heat or activate any plastic being formed therearound. The hollow mandrel support shaft and mandrel may also feed a wire, cable, fiber (optical or electrical), and the hollow mandrel support shaft and mandrel may permit a laser, electron beam, expandable foam or the like to be driven theredown, into any plastic melt entering or passing through a die or mold. The mandrel may be longitudinally advancable and retractable to either the upstream or downstream side of the mold or die. The hollow mandrel may itself may have a longitudinally advancable and retractable conduit therein, for the feeding of a fiber, wire, gas or liquid at any point within the plastic melt, downstream of the mandrel which of course is utilized to shape the inside walls of an extrusion product, in one embodiment may be heavy pipe for water, sewer systems, or thin narrow diameter tubing for medical devices such as catheters, stents or the like. The mandrel may have grooves, either straight or spiralled on its outer surface, the mandrel being held from its proximal support at the proximal end of the machine, either rotatable, longitudinally movable or stationary, by the mandrel support holder.

The thermoplastic reinforced tubular product may be then driven through a downstream outer die, either before or after passage around the mandrel, to provide the outer wall configuration of that tubing being extruded from the machine.

In another preferred embodiment of the present invention, the inner sleeve support may have a plurality of pins extending distally therefrom. Each of the pins may be disposed between the parison tool and the web mesh as the web mesh comes off of the distal end of the inner sleeve support. The pins are arranged to form longitudinally directed conduits (open lumens) within the inside walls of the tubular product as the tubular product is driven from the machine. Pressurized cooling (or heating) fluid or gas may be sent through the inner sleeve support to cool (or heat) effect the tubular product being extruded from the machine. A cooling fluid would help "set" the conduits or lumens generated within the walls of the tubular product as that tubular product is driven downstream from, and off of those pins attached on the distal end of the inner sleeve support.

In a further preferred embodiment, either or both the inner and outer sleeve supports may be movable longitudinally with respect to the inner end of rotating screw shaft and/or die through which tubular product is driven. The mandrel forming tool may also be movable longitudinally with respect to the distal end of the inner sleeve support and/or the die through which the tubular product is driven.

In yet a further preferred embodiment of the present invention, a thermoplastic material (similar or dissimilar to that thermoplastic material being driven through the housing between the screw flight and the inner surface of the housing wall) may be pressurized through the center of the innermost sleeve support to provide an innermost layer of thermoplastic material to the tubular product being generated. This inner material being driven through the inner sleeve support may include electrically conductive, or an electrical insulator. The web mesh may of course be electrically conductive, depending upon the material from which it is being generated. Such a conductive tubular shaft may have uses for heating particular portions of a vessel into which such tubular product is pressed. Those open conduits or lumens generated within the wall of the tubular product may be utilized for providing a pressurizable channel for the inflation of a medical balloon on the end of such a shaft, or for the delivery of medicaments to a particular situs in a vessel in which that shaft is placed.

The invention thus comprises a plasticating machine for the working and forcing of plastic material into a mold or die for the manufacture of a tubular product therethrough, the machine includes an elongated housing having a first or proximal end and a second or distal end. An elongated screw shaft with a screw flight therearound, is rotatably supported in the elongated housing, for the working of plastic between the screw shaft and the elongated housing. At least one pair of coaxial delivery conduits are spaced apart to define an annular delivery channel, the conduits being generally longitudinally arranged axially through an elongated axially disposed bore in the screw shaft, from a proximal end to a distal tip end thereof. A tubular mesh generating, knitting and/or weaving apparatus is arranged at the distal end of the coaxial conduits to generate/weave and feed a tubular reinforcement mesh along the length of the annular delivery channel. A forming tool (mandrel) is supported adjacent the distal end of the innermost conduit of the coaxial conduits, and the mesh is arranged to be movable with respect to the screw shaft to engage any thermoplastic material being driven from between the screw shaft and the barrel housing to form a reinforced tubular product as it is driven through a die at the distal end of the machine.

The forming tool (mandrel) may be movable axially with respect to the coaxial conduits. The innermost conduit may have a thermoplastic generator arranged at its proximalmost end to provide a further thermoplastic delivery channel within the screw shaft. The innermost conduit may have a pressurized fluid generator arranged at its proximalmost end to provide a heat transfer fluid to be passed through the elongated screw shaft and into a tubular product being driven therefrom, for effecting the manufacture of the tubular product. The coaxial conduits may be axially movable within said bore of the screw shaft, so as to permit the mesh being driven from the annular channel therebetween to be moved with respect to the mold at the distal end of the machine. At least one pin may be disposed off of the distalmost end of the innermost of the coaxial conduits to permit an elongated open lumen to be formed in the wall of any thermoplastic material being delivered to a mold adjacent the distal end of the screw shaft.

The invention also includes a method of manufacturing a reinforced plastic tubular product by a plasticating screw machine, comprising the steps of providing an elongated rotatable screw shaft within an elongated barrel housing, the housing having a mold or die adjacent a distal end thereof, arranging a longitudinally directed bore through the elongated screw shaft from a proximal end to a distal end thereof, fitting at least one pair of spaced apart non-rotating coaxial conduits through the bore, the conduits defining an annular delivery channel therebetween, arranging a mesh web generating or weaving apparatus at the proximal end of the annular delivery channel to permit a mesh web to be driven therethrough, generating a mesh web and driving the web through the annular channel between the spaced apart coaxial conduits, and rotating the screw shaft upon feeding of a thermoplastic material into the barrel so as to permit the material to be directed from the screw shaft and into the mesh at the distal end of the screw shaft prior to any plastic being delivered to the mold or adjacent the distal end of the housing. The method includes the steps of inserting a mandrel forming tool adjacent the distal end of the innermost of the coaxial conduits, so as to permit said tubular product to be molded on its inner side as the mesh and thermoplastic are driven through the mold or die, supporting the forming tool on a support shaft arranged through the innermost of the coaxial conduits, supplying a pressurized fluid through the innermost of the coaxial conduits to cool the thermoplastic material being driven adjacent the distal end thereof, supplying a thermoplastic material through the innermost of the coaxial conduits so as to add further plastic material to the innerside of the mesh being driven from the distalmost end of the coaxial conduits, and attaching at least one pin onto the distalmost edge of the innermost of the coaxial conduits so as to generate a lumen in the tubular wall of any thermoplastic material being driven therepast and being made into a tubular product.

Thus there has been shown, a unique plastic extrusion machine, wherein screw permits the manufacture of a reinforced flexible (or rigid) tubular product through a die or a mold, which tubular product may have unique features not known in the industry.

BRIEF DESCRIPTION OF THE DRAWINGS

The objects and advantages of the present invention, will become more apparent, when viewed in conjunction with the following drawings, in which:

FIG. 1 is a side elevational view, in section, showing a plasticating screw shaft and multiple conduit assembly therewithin for treatment of thermoplastic material, according to the principles of the present invention;

FIG. 2 is an end view of one embodiment of a tube product made according to the principles of the present invention.

DESCRIPTION OF THE PREFERRED EMBODIMENTS

Figure 3A:
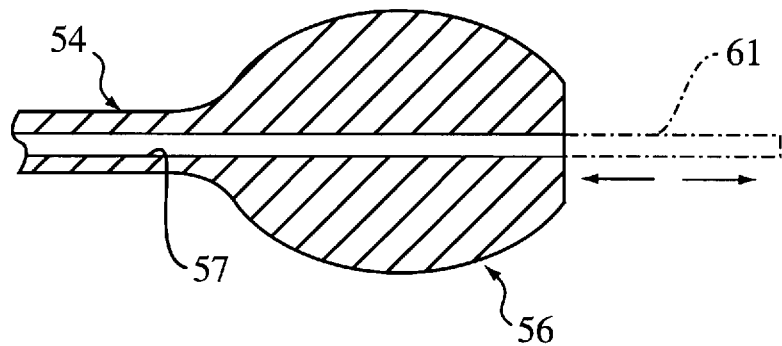
FIGS. 3 a, b and c show side elevational views of three embodiments of a forming tool of the present invention.

Referring now to the drawings in detail, and particularly to FIGS. 1 and 2, there is shown the present invention which relates to a plasticating screw machine 10 for treating of thermoplastic material and pressurizably directing that thermoplastic material into an extrusion die 12 thereadjacent.

The plasticating screw machine 10 of the present invention comprises an external barrel shaped housing 14 having an elongated screw shaft 16 rotatively supported therewithin. The housing 14 and the screw shaft 16 have a proximal or first end 18 and a distal or a second end 20. The screw shaft 16 is rotatively empowered at the proximal first end 18 of the housing 14 by a motor drive means 22 thereattached. At least one material in-feed supply hopper 24 may be arranged through the housing 14 near the proximal end 18 thereof.

The screw shaft 16 has a bore 26 extending completely therethrough along its longitudinal axis, from its proximalmost end to its distalmost end. The bore 26 has a wall surface 28 to define a further material moving path.

A non-rotational outer sleeve support 32 may be arranged within the bore 26 of the screw shaft 16, extending preferably from the proximal end 18 of the housing 14, to the distal end 20 of the screw shaft 16.

An inner tubularly shaped sleeve support 36 may be arranged coaxially within the outer sleeve support 32 within the bore 26 of the screw shaft 16. A tubular web generating or weaving apparatus 40 (for example, similar to that for manufacturing nylon hosiery or the like), is disposed around the periphery of the proximal end of the inner sleeve support 36, so as to generate, weave or knit a tubular web of mesh reinforcement 42 thereat, the mesh web 42 being preferrably formed of metal wire of stainless steel, nickel-titanium or an alloy thereof, or plastic reinforcing film with or without openings therein, which web mesh 42 is directed into the annular path 44 spaced between the inner sleeve support 36 and the outer sleeve support 32.

The mesh web 42 extends into and travels through the bore 26 of the plasticating screw screw shaft 16, within the annular channel 44 defined by the inner and outer support sleeves 36 and 32, and is driven from the distal end of those inner and outer sleeve supports 36 and 32 and out of the distal discharge end of the screw shaft 16 and screw housing 14, which includes the flow path of thermoplastic material "M" being worked between the helical screw flight 50 on the screw shaft 16 and the inner walls of the barrel housing 14. The wire mesh 42 and the thermoplastic material "M" mix into the desired tubular shape of an extruded shaft or tube "T". A forming tool or mandrel support shaft 54 extends through the center of the inner sleeve support 36, with a mandrel forming tool 56 on its distalmost end thereof. The mandrel forming tool 56 itself preferably extends beyond the distalmost end of the inner sleeve support 36, to provide the needed shape to the inner surface of the tubing "T" being extruded from the machine 10. The thermoplastic reinforced tubular product "T" may be then driven through the downstream outer die 12, to provide the outer wall configuration of that tubing "T" being extruded from the machine 10.

In another preferred embodiment of the present invention, the inner sleeve support 36 may have a plurality of pins 60 extending distally therefrom, as shown in FIG. 1. Each of the pins 60 may be disposed between the parison tool 56 and the web mesh 42 as the web mesh 42 comes off of the distal end of the inner sleeve support 36. The pins 60 are arranged to form longitudinally directed conduits (open lumens) 66 within the walls of the tubular product "T" as the tubular product "T" is driven from the machine 10. The tubular product "T" may be seen in an end view in FIG. 2. Pressurized cooling (or heating) fluid or gas may be sent through the inner sleeve 36 support to provide a cool (or heat) effect to the tubular product "T" being extruded from the machine 10. A cooling fluid would help "set" the conduits or lumens 66 generated within the walls of the tubular product "T" as that tubular product "T" is driven downstream from, and off of those pins 60 attached on the distal end of the inner sleeve support 36.

In a further preferred embodiment, either or both the inner and outer sleeve supports 32 and 36 may be movable longitudinally with respect to the inner end of rotating screw shaft 16 and/or die 12 through which tubular product "T" is driven. The mandrel forming tool 56 may also be movable longitudinally with respect to the distal end of the inner sleeve support 36 and/or the die 12 through which the tubular product "T" is driven.

In yet a further preferred embodiment of the present invention, a second thermoplastic material "MM" (similar or dissimilar to that thermoplastic material "M", driven through the housing 14 between the screw flight 50 and the inner surface of the housing 14) may be pressurized through the center of the innermost sleeve support 36 to provide an innermost layer of thermoplastic material "MM" to the tubular product "T" being generated. This inner material "MM" being driven through the center of the inner sleeve support 36 may be electrical conductor, or an electrical insulator. The web mesh 42 may of course be electrically conductive, depending upon the material from which it is being generated or woven. Such a conductive tubular shaft may have uses for heating particular portions of a vessel into which such tubular product is pressed. The open conduits or lumens 66 generated within the wall of the tubular product "T" may be utilized to provide one or more channels for the introduction of inflation fluid to a medical balloon on the end of such a shaft, or for the delivery of medicaments through such lumens 66 to a particular situs in a vessel in which that shaft is placed.

Figure 3B:
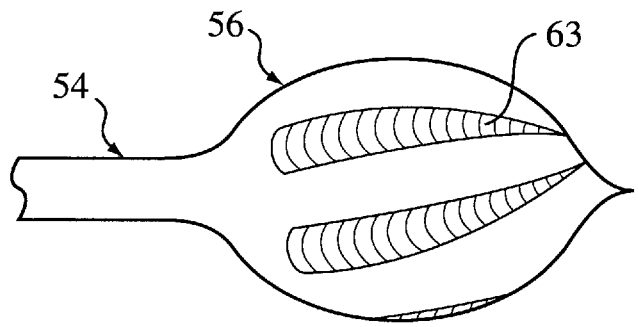
Figure 3C:
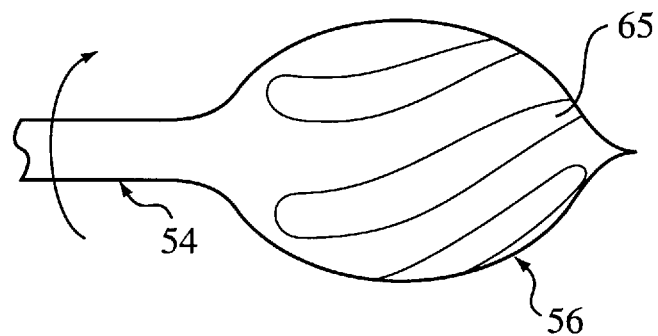

In several further embodiments shown in FIGS. 3a, 3b, and 3c, the mandrel support shaft 54 and attached mandrel 56, may both have an open center bore 57, to permit the supply of a pressurized fluid downstream therein, to cool, heat or activate any plastic being formed therearound, from a pressure source 59, as shown in FIG. 1. The mandrel support shaft 54 with an open bore 57 therethrough and mandrel 56 may also feed a wire, cable, fiber (optical or electrical), and the hollow mandrel support shaft and mandrel may permit a laser, electron beam, expandable foam or the like, supplied from a proper holder/source 59, to be driven theredown, into any plastic melt "M" entering or passing through a die or mold. The mandrel 56 may be longitudinally advancable and retractable to either the upstream or downstream side of the mold or die 12, to permit different spacing therebetween, thus permitting the wall thickness to be changed accordingly. The hollow mandrel 56, may itself may have a longitudinally advancable and retractable conduit 61 therein, as shown in phantom in FIG. 3a, for the feeding of a fiber, wire, gas or liquid at any point within the plastic melt, downstream of the mandrel 56. The mandrel 56 may be utilized to shape the inside walls of an extrusion product, which in one embodiment may be heavy stiff pipe for water, sewer systems, or in another preferred embodiment, may be flexible, thin narrow diameter tubing for medical devices such as catheters, stents or the like. The mandrel 56, as shown in FIG. 3b, may have straight grooves 63, or spiralled grooves 65 on its outer surface, the mandrel 56 being held from its proximal support at the proximal end of the machine, either rotatable, longitudinally movable or stationary, by the mandrel holder/supply source 59. The grooves 63 and 65 permit the tubular product being formed to have strengthening surface extensions emplaced on its inner wall surface.

Thus is shown a plastication machine combination for the production of reinforced flexible tubing or rigid pipe is shown, having the features of multiple layers, electrical/ optical capabilities, displacable mandrel with respect to the screw and or die/mold, in a manner novel in the art.

We claim:

1. A method of manufacturing a reinforced thermoplastic tubular product by a plasticating screw machine, comprising the steps of:

providing an elongated rotatable screw shaft within an elongated barrel housing, and a mold or die adjacent a distal end of said housing;

arranging a longitudinally directed bore through said elongated screw shaft from a proximal end to a distal end thereof;

fitting at least one pair of spaced apart, non-rotating coaxial conduits through said bore, said conduits comprising an inner conduit and an outer conduit having proximal and distal ends, an annular delivery channel being defined between said inner and outer conduits;

arranging a mesh web generating apparatus at a proximal end of said annular delivery channel to permit a mesh web to be driven through said annular delivery channel;

generating a mesh web and driving said web through said annular channel between said spaced apart coaxial conduits; and feeding thermoplastic material into said barrel and rotating said screw shaft so as to plasticate said thermoplastic material and permit said material to be directed from said screw shaft and into said mesh at a distal end of said screw shaft prior to said thermoplastic material being delivered to said mold or die adjacent said distal end of said housing to form said reinforced thermoplastic tubular product.

2. The method as recited in claim 1, including the step of:

inserting a forming tool adjacent the distal end of said inner conduit, so as to permit said tubular product to be molded on its inner side as said mesh and thermoplastic are driven through said housing.

3. The method as recited in claim 2, including the step of:

supporting said forming tool on a tool support shaft arranged through said inner conduit.

4. The method as recited in claim 1, including the step of supplying a pressurized fluid through said inner conduit to cool the thermoplastic material being delivered to said mold or die.

5. The method as recited in claim 1, including the step of:

supplying a thermoplastic material through said inner conduit so as to add further thermoplastic material to the innerside of said mesh being driven from said annular delivery channel.

6. The method as recited in claim 1, including the step of:

attaching at least one pin onto the distalmost edge of one of said conduits so as to generate a lumen in the tubular wall of said thermoplastic material being driven into said mold or die.

7. The method as recited in claim 3, including the step of:

arranging said forming tool on the distal end of said tool support shaft and providing a bore through said tool support shaft and forming tool to permit a gas, liquid, solid or an energy means to be delivered from a proximal end of said tool support shaft to a distal end of said forming tool, and into said thermoplastic material.

* * * * *